US008530237B2

(12) United States Patent
Takahashi et al.

(10) Patent No.: US 8,530,237 B2
(45) Date of Patent: Sep. 10, 2013

(54) METHOD FOR CULTURING ANIMAL HEPATOCYTE

(75) Inventors: Ryosuke Takahashi, Kawagoe (JP); Akiko Hisada, Kawagoe (JP); Hiroshi Sonoda, Tsurugashima (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 13/143,569

(22) PCT Filed: Jan. 8, 2009

(86) PCT No.: PCT/JP2009/050140
§ 371 (c)(1),
(2), (4) Date: Jul. 7, 2011

(87) PCT Pub. No.: WO2010/079602
PCT Pub. Date: Jul. 15, 2010

(65) Prior Publication Data
US 2011/0269232 A1 Nov. 3, 2011

(51) Int. Cl.
*C12N 5/02* (2006.01)
*A01N 63/00* (2006.01)

(52) U.S. Cl.
USPC ........... 435/402; 424/93.7; 977/923; 977/782

(58) Field of Classification Search
None
See application file for complete search history.

(56) References Cited

U.S. PATENT DOCUMENTS

| | | | |
|---|---|---|---|
| 2004/0125266 | A1 | 7/2004 | Miyauchi et al. |
| 2006/0183222 | A1 | 8/2006 | Kuwabara et al. |
| 2007/0299537 | A1 | 12/2007 | Sudo et al. |
| 2008/0057578 | A1 | 3/2008 | Kuwabara et al. |
| 2008/0215073 | A1 | 9/2008 | Iwanaga et al. |

FOREIGN PATENT DOCUMENTS

| | | |
|---|---|---|
| CN | 101050418 A | 10/2007 |
| JP | 7-274952 | 10/1995 |
| JP | 2004-170935 | 6/2004 |
| JP | 2006-223197 | 8/2006 |
| JP | 2008-54566 | 3/2008 |
| JP | 2008-199962 | 9/2008 |
| WO | WO 2005/047496 A1 | 5/2005 |

OTHER PUBLICATIONS

Alexandru I. Musat, Carol A. Sattler, Gerald L. Sattler, and Henry C. Pitot Reestablishment of cell polarity of rat hepatocytes in primary culture, Hepatology, 1993, 18(1):198-205.*
Cima et al., Biotechnology and Bioengineering, Hepatocyte culture on biodegradable polymeric subsstrates, 38:145-158, 1991.*
S. M. Hutson, C. Stinson-Fisher, R. Shiman, and L. S. Jefferson, Regulation of albumin synthesis by hormones and amino acids in primary cultures of rat hepatocytes, Am. J. Physiol. 252 (Endocrinol. Metab. 15): E291-E298, 1987.*
J. Landry et al., Spheroidal Aggregate Culture of Rat Liver Cells: Histotypic Reorganization, Biomatrix Deposition, and Maintenance of Functional Activities, the Journal of Cell Biology, Sep. 1985, pp. 914-923, vol. 101.
Leoni A. Kunz-Schughart et al., The Use of 3-D Cultures for High-Throughput Screening: The Multicellular Spheroid Model, Journal of Biomolecular Screening 9(4); 2004, pp. 273-285.
James C.Y. Dunn, et al., Hepatocyte function and extracellular matrix geometry: long-term culture in a sandwich configuration, The Faseb Journal, Feb. 1989, pp. 174-177, vol. 3.
Shinobu Nomura et al, Nanopillar sheets as a new type of cell culture dish: detailed study of HeLa cells cultured on nanopillar sheets, the Japanese Society for Artificial Organs, 2006.
Choi et al., Cell Growth as a Sheet on Three-Dimensional Sharp-Tip Nanostructures, Journal of Biomedical Materials Research Part A, vol. 89A, No. 3, Jun. 1, 2009, pp. 804-817.
Nomura et al., Cell Culture on Nanopillar Sheet: Study of HcLa Cells on Nanopillar Sheet, Japanese Journal of Applied Physics, vol. 44, No. 37, Sep. 1, 2005, pp. 1184-1186.
Fukuda et al., Novel Hepatocyte Culture System Developed Using Mcirofabrication and Collagen/Polyethylene Glycol Microcontact Printing, Biomaterials, Elsevier Science Publishers BV, vol. 27, No. 7, Mar. 1, 2006, pp. 1061-1070.
Takahashi et al., Formation of Hepatocyte Spheroids with Structural Polarity and Functional Bile Canaliculi Using Nanopillar Sheets, Tissue Engineering Part A, vol. 16, No. 6, Jun. 1, 2010, pp. 1983-1995.
EP Office Action of Appln. No. 09837490.3 dated Mar. 23, 2012 in English.
Chin J Exp Surg, Jan. 2003, vol. 20, No. 1, p. 23.
G. Michalopoulos et al., Primary Culture of Parenchymal Liver Cells on Collagen Membranes, Morphological and Biochemical Observations, Experimental Cell Research 94, 1975, pp. 70-78 in English.

* cited by examiner

*Primary Examiner* — Jennifer Pitrak McDonald
*Assistant Examiner* — Qing Xu
(74) *Attorney, Agent, or Firm* — Antonelli, Terry, Stout & Kraus, LLP.

(57) ABSTRACT

Provided are a technique for easily forming a spheroid by three-dimensionally culturing hepatocytes, and a technique for forming a spheroid having a higher expression level of a transporter MRP2 playing a role of biliary excretion than that of a conventional method. In order to solve the above-described problems, the present inventors have found out a condition under which hepatocytes easily form the spheroid on a nanopillar sheet. More specifically, this is related to a concentration of Type I collagen coated onto the NP sheet. Also, they have found out a condition under which an expression level of a gene related to the excretion of the formed spheroid is improved. More specifically, after the spheroid is previously formed, a biological matrix is overlayered thereon.

9 Claims, 9 Drawing Sheets

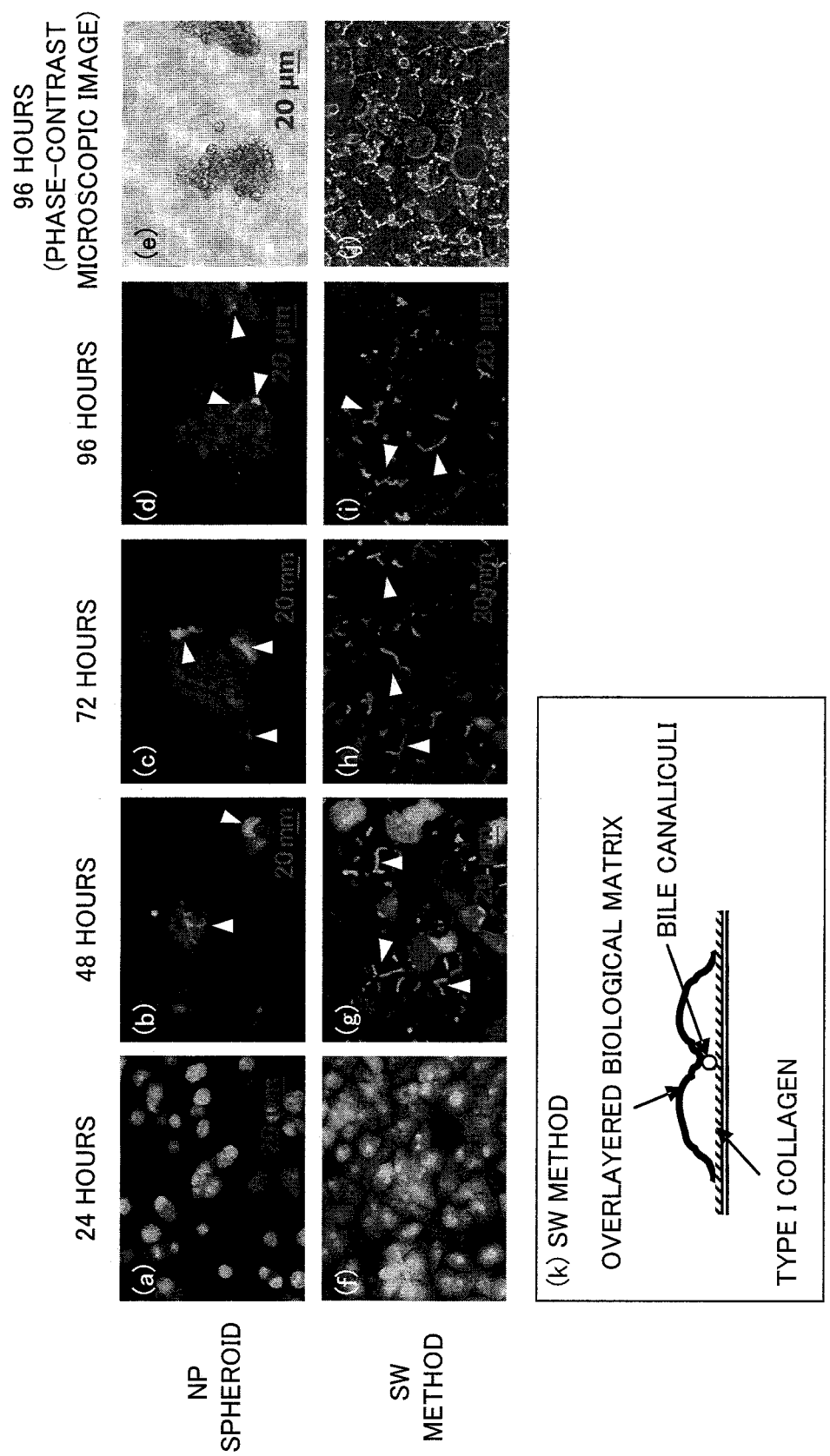

METHOD FOR CULTURING ANIMAL HEPATOCYTE

TECHNICAL FIELD

The present invention relates to a method for forming a three-dimensional spheroid which is a hepatocyte mass or a tissue-like structure by culturing animal hepatocytes with using a culture substratum.

BACKGROUND ART

A standard process of drug development can be roughly divided into three steps. A first step is, after investing medicinal needs and selecting a disease to be a target of the drug development, to search an effective substance for the disease, and discover (screen) an objective drug candidate. Subsequently, a second step is to verify the effectiveness and safety for the diagnosis and treatment of the disease targeted by the drug candidate through a nonclinical trial and a clinical trial, summarize its evaluation result in a new-drug application, and obtain its approval from a government. And, a third step is to sell the approved drug in a market to be used for medical care. In this drug-discovery process, as seen from a viewpoint such that a cost for its research and development is high, it has been reported that an amount equivalent to 30%, in some cases, 50% of a total research and development cost is spent on animal experiments.

Animal experiments are used in nonclinical trials, some clinical trials, or initial screening. Therefore, under a recent circumstance that a development cost per one item of the new drug almost reaches 100 billion yen, by developing an alternative low-cost test method instead of the animal experiments, a cost reduction effect in suppressing the research and development cost is expected. Further, also from a viewpoint of animal welfare and protection, particularly as seen from a recent trend in EU, reduction of the animal experiments has been already socially such a large stream that cannot be returned. Still further, it has been pointed out that an in vitro alternative method with using cells is advantageous for figuring out an action mechanism of in-vivo kinetics of a drug or a chemical compound, which is difficult to be understood by conventional animal experiments, more particularly, for evaluating metabolism, detoxification, and hepatic duct excretion in a liver, which is one of important indicators (in Non-patent Document 1).

Under such a background, approaches to alternative methods with using cells have been actively taken in the past. However, many methods have a limitation in the prediction of clinical reactions. A reason for this limitation has been considered that, in these culture methods, cells do not have a structure mimicking an actual in-vivo structure (in Non-patent Document 2). Therefore, the construction of a three-dimensional structure closer to a living body and the establishment of an in vitro assay system with using the structure have been required. More particularly, an in vitro assay system with using hepatocytes is highly expected, and an evaluation system for metabolism or bile canalicular excretion in a liver, which is one of important screening indicators, has been required. The bile canaliculus is a space bounded by two or more hepatocytes, and closes an intercellular space by a tight junction to prevent leakage of bile. The liver transports bile and metabolites from the hepatocytes into the bile canaliculi with using an ATP-dependent transporter expressed in a cell membrane. As a technique for measuring such a hepatic duct excretion, a sandwich method is cited (in Non-patent Document 3). However, practical use of the method showing a sufficient performance has not been achieved yet.

As a device for achieving the three-dimensional structure of the cell, a nanopillar cell culture sheet (hereinafter, referred to as a "nanopillar sheet" or a "NP sheet") is cited (in Patent Document 1). The NP sheet is a scaffolding material for cell culture or tissue culture, which is produced by applying a microfabrication technology such as a nano-imprint technology. A feature of the nanopillar sheet is that, by using an artificially-designed fine three-dimensional structure as the scaffolding material, an effect as a device for three-dimensional culture can be expected. Some reports for the cell culture with using the nanopillar sheet have been made (in Patent Documents 2 and 3).

Patent Document 1: Japanese Patent Application Laid-Open Publication No. 2004-170935
Patent Document 2: Japanese Patent Application Laid-Open Publication No. 2006-223197
Patent Document 3: Japanese Patent Application Laid-Open Publication No. 2008-054566
Non-Patent Document 1: J. Cell Biol. 101: 914-923 (1985)
Non-Patent Document 2: J. Biomol. Screen. 9: 273-285 (2004)
Non-Patent Document 3: FASEB J 3: 174-177 (1989)

DISCLOSURE OF THE INVENTION

Problems to be Solved by the Invention

A conventional sandwich culture method (hereinafter, referred to as SW culture) is a method for a two-dimensional culture by overlayering Type I collagen on a bottom surface of the hepatocyte and a biological matrix on a top surface of the hepatocyte to sandwich the cell by these two types of substances, and has a feature that the metabolites excreted into the hepatic duct can be quantitated. However, in an in-vitro based SW culture, a dynamic range of the measurement is narrow, and therefore, there is a problem that minute variations cannot be measured. It is considered that this is because an essential cell function of the hepatocyte taken outside once from an inside of the living body is decreased, and the number of bile canaliculi formed in a structure reconstructed in a culture dish is smaller than that inside the living body.

Accordingly, by the three-dimensional culture of the cell, resulting in close to an in vivo tissue structure, a trend of solving the problem has been rapidly spread. More specifically, the culture with using the NP sheet has been attempted. However, regarding the cell culture with using the NP sheet, Patent Documents 2 and 3 describe a three-dimensional culture of fat cells or culture of nerve cells. However, they have not considered the culture of the hepatocytes and do not specifically describe the hepatocyte culture. Therefore, if the methods of Patent Documents 2 and 3 are applied to the hepatocyte culture, there is a problem that a desired spheroid is not formed.

From these reasons, a preferred aim of the present invention is to provide a method for generating a three-dimensional hepatocyte spheroid having a structure and a function close to those of a living body with using an NP sheet.

Means for Solving the Problems

In order to solve the above-described problems, a condition under which the hepatocytes form the spheroid on the nanopillar sheet has been found out. More specifically, Type I collagen is coated on the NP sheet. Also, a condition under which a gene expression level for excretion of the formed spheroid is improved has been found out. More specifically, after previously forming the spheroid, the biological matrix is overlayered thereon.

Effects of the Invention

By applying the present invention, the spheroid which is the hepatocytes having the three-dimensional structure can be easily formed on the nanopillar sheet. In the formed spheroid, expression of a transporter MRP2 playing a role of biliary excretion is higher than that in a conventional method, and the spheroid has biliary excretion capacity closer to that of the living body. By using such a spheroid, measurement with a wider dynamic range capable of measuring a small amount of the excretion can be achieved. By widening the dynamic range of the measurement, the measurement can be applied to pharmacokinetic tests in the process of drug discovery.

BRIEF DESCRIPTIONS OF THE DRAWINGS

FIGS. 5A to 5K are views showing results of measurement of biliary excretion with using CDFDA;

SYMBOL DESCRIPTION

Figure 1A:
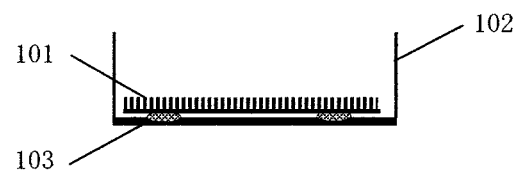
FIGS. 1A to 1F are diagrams showing culturing steps of hepatocyte spheroid culture.

| 101: | NP sheet |
|---|---|
| 102: | cell culture dish |
| 103: | adhesive |
| 104: | Type I collagen solution |
| 105: | decompression container |
| 106: | decompression pump |
| 107: | flushing saline (Phosphate buffered saline (−); hereinafter, referred to as PBS(−)) |
| 108: | culture medium |
| 109: | hepatocyte |
| 110: | hepatocyte spheroid |
| 111: | decompression chamber |
| 112: | carry-in/out part of decompression unit |
| 113: | open/close valve |
| 114: | connection unit |
| 115: | decompression pump |
| 116: | incubator |
| 117: | liquefied carbon dioxide gas tank |
| 118: | deionized water |
| 119: | carry-in part |
| 120: | carry-out part |
| 121: | inner carry-in part |
| 122: | inner carry-out part |
| 123: | storage room |

BEST MODE FOR CARRYING OUT THE INVENTION

A best mode for carrying out a method for forming a three-dimensional spheroid which is a hepatocyte mass or a tissue-like structure by culturing hepatocytes with using a culture substratum is described in detail as follows.

Example 1

In Example 1, a step for forming the hepatocyte spheroid on the NP sheet is described.

<Preparation of Hepatocytes>

The preparation of hepatocytes follows an in-situ collagenase perfusion method. The details are as follows. A male Fisher 344 rat (7 to 10 weeks old) is subjected to laparotomy under pentobarbital anesthesia, a catheter is inserted into a portal vein, and a pre-perfusion solution (Hanks' solution without containing $Ca^{2+}$ and $Mg^{2+}$ and with containing EGTA) is injected thereinto. At the same time, an inferior vena cava in a lower portion of the liver is incised to release blood. Next, a thoracic cavity is opened, an inferior vena cava entering a right atrium is incised, and the inferior vena cava in the lower portion of the liver is clamped to perform the perfusion. After sufficient blood removal from the liver is confirmed, the perfusion is stopped. A perfusion solution is replaced with a collagenase solution, and the perfusion is performed. In this example, the perfusion is performed with using a Hanks' solution containing 0.05% collagenase. However, the invention is not limited to the solution. After digestion of an intercellular tissue by the collagenase is confirmed, the perfusion is stopped. The liver is cut and separated, is sliced in a cooled Hanks' solution, and is dispersed by pipetting to be cells. Subsequently, undigested tissues are removed by gauze filtration. A cell suspension is centrifuged at 50 G for 1 minute repeatedly several times to remove nonparenchymal cells. Subsequently, with using an isotonic percoll solution, damaged hepatocytes are removed by centrifugation at 500 G for 5 minutes. A survival rate of the obtained hepatocytes is measured by the trypan blue exclusion method, and hepatocytes with the survival rate of 85% or higher are used for the culture. Here, the hepatocytes with the survival rate of 85% or higher are used for the culture. However, it is needless to say that the invention is not necessarily limited to the condition. Also, the preparation of the hepatocytes is not necessarily limited to the in-situ collagenase perfusion method.

Further, human hepatocytes can be also prepared by the same method.

<Preparation of NP Sheet on which Type I Collagen is Coated>

An NP sheet (101) is attached on a bottom surface of a culture dish (102) (FIG. 1A). The attaching of the NP sheet (101) is not particularly limited, and may be performed by, for example, an instant adhesive or a double-sided tape. Also, a container on which the NP sheet (101) is attached is not particularly limited, and may be a commercially-available dish for cell culture or a chamber slide. The Example 1 shows an example that the NP sheet (101) is attached on a commercially-available cell culture dish (102) with an instant adhesive (103). As the NP sheet (101), a plurality of NP sheets having a top of a head with a predetermined diameter described later are used.

Figure 1B:
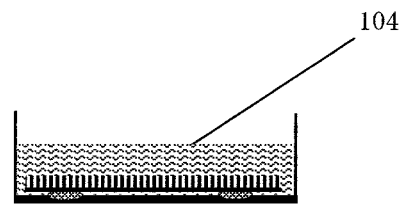

Next, 1 to 1.5 mL of a diluted solution (Type I collagen solution) 104 obtained by diluting the Type I collagen dissolved in a weak acid solution by sterilized water so as to have a predetermined concentration is added to the NP sheet (FIG. 1A) attached on the chamber slide (FIG. 1B).

Figure 1C:
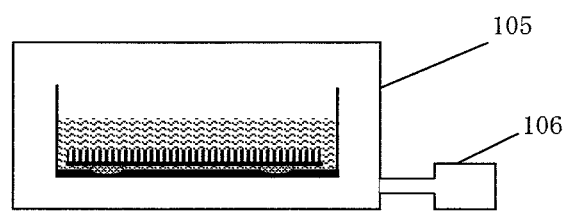

Next, in order to completely adsorb the added Type I collagen on the NP sheet, a decompression operation is performed inside a decompression container 105 by a decompression pump 106 (FIG. 1C). The decompression operation is performed at 0.04 atmosphere or lower. While the decompression time is not particularly limited, the decompression operation in this example is performed for 10 minutes. An apparatus used for the decompression is not particularly limited. Here, a range of the predetermined concentration of the diluted solution is $1/10^6$% (W/V) or higher and $1/10^8$% (W/V) or lower. While the concentration is not necessarily limited to this range, if the concentration is higher or lower than the range, there is a possibility that the spheroid is not formed.

Figure 1D:
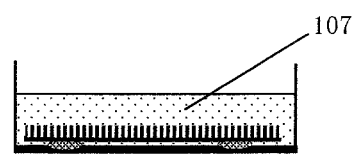

Finally, the Type I collagen is removed, and PBS(−) 107 is added (FIG. 1D). This process is performed three times to wash the Type I collagen.

<Culture of Hepatocytes>

Figure 1E:
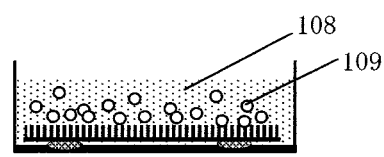
Figure 1F:
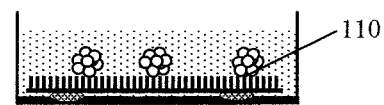
Figure 2:
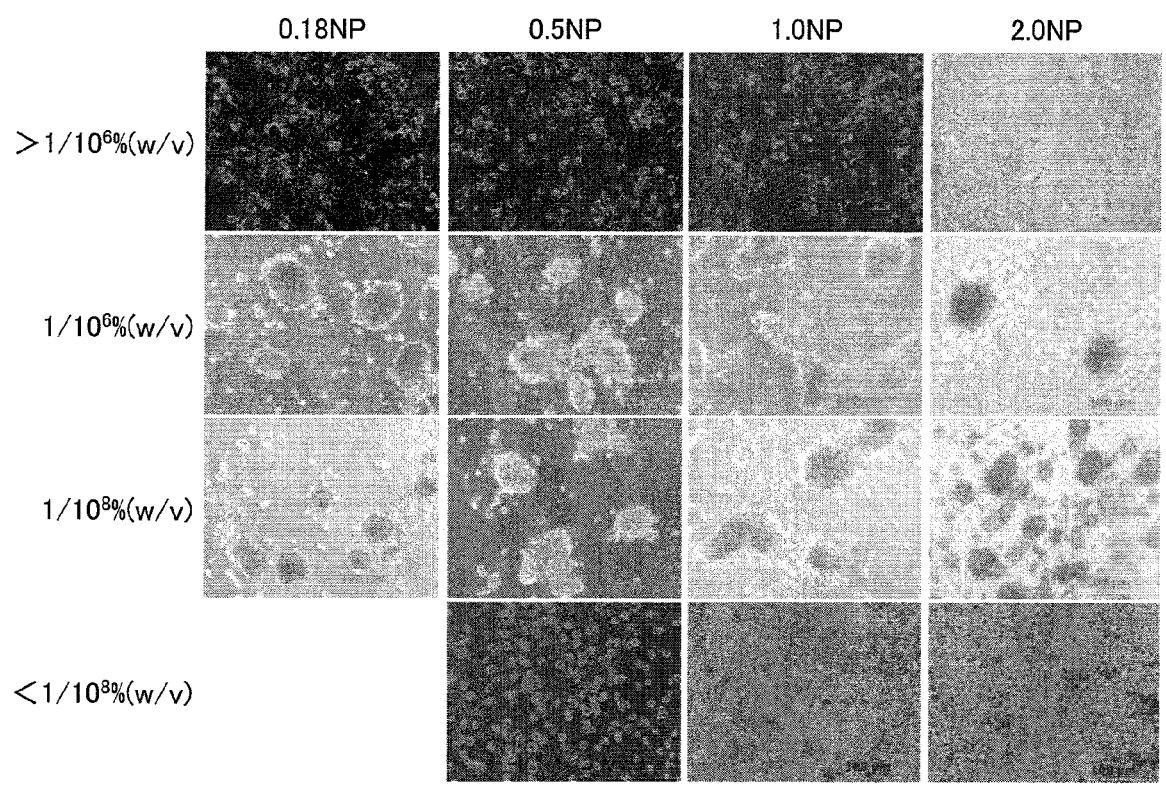
FIG. 2 is views showing phase-contrast microscopic images of hepatocytes cultured on four types of an NP sheet coated by a Type I collagen solution as changing its concentration.

The hepatocytes 109 prepared by the in-situ collagenase perfusion method as described above are suspended in a culture medium 108, and are seeded on the NP sheet which is similarly prepared as described above and on which the Type I collagen has been coated (FIG. 1E). While the culture medium is not particularly limited, a Williams E medium containing a culture medium containing serum (FCS), insulin, and dexamethasone (hereinafter, refereed to as culture medium (10% FCS+)) is used. In this example, more particularly, a Williams E medium containing 10% FCS, 8.6 nM insulin, and 255 nM dexamethasone is used. After the seeding, the culture is started under a condition of 5% $CO_2$ at 37° C. with using a $CO_2$ incubator. After passing 18 hours or longer, a first culture-medium replacement is performed, and then, the culture-medium replacement is performed every 24 hours. While the culture media used for the culture after passing 18 hours from the seeding are not particularly limited, a culture medium (hereinafter, referred to as culture medium (FCS−)) obtained by removing the FCS from the culture medium (10% FCS+) is used in this example. Also, while the seeding density of the hepatocytes is $1 \times 10^5$ cells/ml in this example, the invention is not limited to this concentration. Here, the NP sheet used for the culture is four types including: (1) an NP sheet with a diameter of a top of a head of 0.18 μm (hereinafter, referred to as 0.18 NP); (2) an NP sheet with that of 0.5 μm (hereinafter, referred to as 0.5 NP); (3) an NP sheet with that of 1.0 μM (hereinafter, referred to as 1.0 NP); and (4) an NP sheet with that of 2.0 μm (hereinafter, referred to as 2.0 NP). Also, the concentration of the Type I collagen added to the NP sheet is four types including: (1) $1/10^6$% (W/V) or higher, (2) $1/10^6$% (W/V), (3) $1/10^5$% (W/V), and (4) $1/10^5$% (W/V) or lower. The culture is performed under the total 16 types of conditions. Depending on the conditions, a spheroid 110 is formed (FIG. 1F). The results of the culture under the 16 types of conditions are as shown in FIG. 2, and an optimal condition for forming the spheroid is determined by the results. According to the results, it is found out that, regardless of using any NP sheet, the condition that the Type I collagen concentration is $1/10^6$% (W/V) or higher and $1/10^8$% (W/V) or lower is most preferable.

Example 2

In Example 2, the effectiveness of the NP hepatocyte spheroid described in the Example 1 is evaluated. Hereinafter, for each evaluation method, an evaluation procedure and an evaluation result are described in this order.

<Immunostaining>

Immunostaining is performed in order to show that the structure of the formed hepatocyte spheroid is close to the structure of the in-vivo liver tissue. Focused molecules are E-cadherin which is a cell-cell (intercellular) adhesion protein and actin which is a cytoskeletal protein. The E-cadherin is one of membrane proteins playing a role of the cell-cell adhesion binding, and is a protein essential for constructing a tissue having a higher dimensional structure by binding cells with each other. Also, the actin is a cytoskeletal protein providing a physical support to cells when the cells adhere to each other to form the higher dimensional structure. The expression of these two proteins is an index essential to show that the tissue is established as the in-vivo tissue.

The procedure of the immunostaining is described below. First, as following the Example 1, the hepatocyte spheroid is formed with using the NP sheet on which the Type I collagen has been coated (hereinafter, referred to as NP normal culture). In this example, from the results of the Example 1, the spheroid is formed by coating $1/10^6$% (W/V) of the Type I collagen on the 2.0 NP that have particularly developed the actin which is a target skeletal protein and the E-cadherin which is a target cell-cell adhesion protein, and have constructed a nearly spherical spheroid. However, the invention is not necessarily limited to this condition. The formed spheroid is washed with the PBS(−) three times, and fixed. While the spheroid is fixed for 15 minutes with using 4% paraformaldehyde in this example, the invention is not necessarily limited to this method. The spheroid is washed with the PBS (−) three times, and is dipped in a nonionic surfactant for 5 minutes to destroy the cell membrane. While 0.5% Triton X is used in this example, the invention is not necessarily limited to this substance. After washing the spheroid with the PBS(−) three times, blocking is performed. While the blocking is performed by dipping the spheroid in 1% FBS (Fetal Bovine Serum) for 30 minutes in this example, the invention is not necessarily limited to this method. Then, a primary antibody is acted. While a monoclonal rabbit anti-human E-cadherin antibody is acted in this example, the immune animal species is not limited to a rabbit, and may be also, for example, a mouse or a goat. Also, while action temperature and time for the primary antibody are at 4° C. for one day and night in this example, the invention is not limited to them. Subsequently, after washing the spheroid with the PBS(−) containing a nonionic surfactant, it is washed only with the PBS(−). While a substance of 0.05% Tween20/PBS(−) is used in this example, the invention is not limited to this substance. Then, a fluorescein-added (labeled) secondary antibody is acted. While an FITC-added anti-rabbit IgG antibody is acted in this example, the immune animal species is not limited to a rabbit, and may be also, for example, a mouse or a goat. Further, while action temperature and time is at 37° C. for one hour in this example, the invention is not limited to this method. Subsequently, the washing is performed with using the same method. Next, actin fibers are stained. While rhodamine-added phalloidin is acted at a room temperature for 5 minutes in this example, action time is not limited to this. The spheroid is washed with the PBS(−) once, and nuclear staining is performed. While "Hoechst33342" is acted at the room temperature for 5 minutes in this example, the invention is not limited to this method. Finally, the spheroid is washed with Milli-Q water, and is sealed.

Here, for comparison, immunostaining is performed to the hepatocytes obtained by conventional plane culture to verify the expression levels of the E-cadherin and the actin. The conventional plane culture is performed as follows. The hepatocytes are suspended and seeded in the above-mentioned culture medium at a density of $1 \times 10^5$ cells/ml on a commercially-available collagen-coated culture dish. After passing 18 hours or longer from the seeding, a first culture-medium replacement is performed, and then, the culture medium is replaced every 24 hours. The culture medium used for the culture after passing 18 hours from the seeding is as described above (hereinafter, referred to as plane culture). To cells obtained by such a plane culture, the immunostaining is performed by the method as described above.

Similarly, for comparison, the immunostaining is performed also to a frozen liver tissue slice to verify the expression levels of the E-cadherin and the actin. A method for preparing the frozen slice is performed as follows. The method is the same as that in the Example 1 up to the step of, after the laparotomy of the rat, removing the blood with using the pre-perfusate. Then, a part of the liver is cut off, an embedding agent is added thereto, and the liver is frozen in a freezer at −80° C. With using the frozen sample, the slice is produced in a freezing microtome method. The immunostaining is performed to such an obtained frozen slice by the above-described method.

Figure 3:
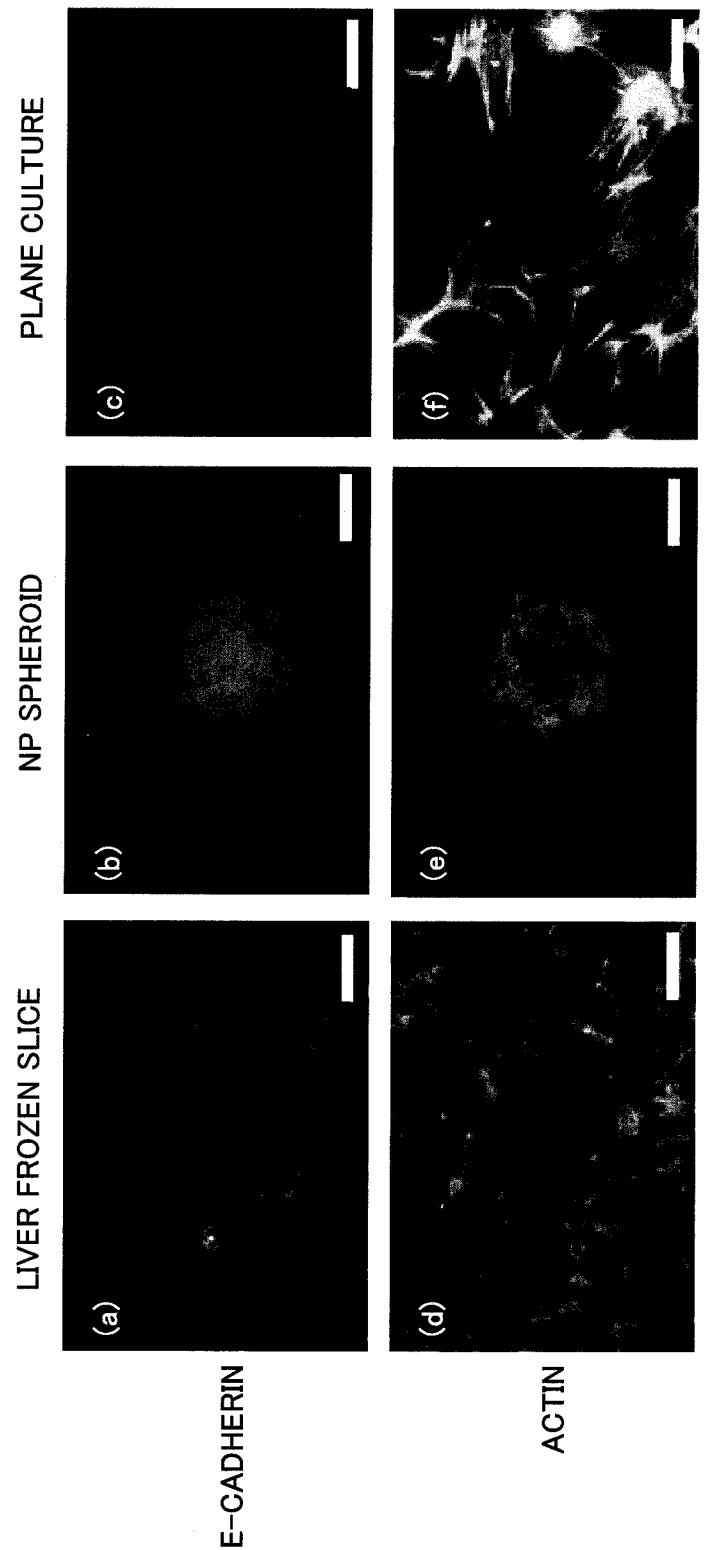
FIGS. 3A to 3F are views showing immunohistochemistry of a liver frozen tissue slice, an NP spheroid, and a plane-cultured cell.

FIG. 3 shows the results of the immunostaining for the three types including: the NP spheroid; the plane culture; and the frozen slice, which are prepared as described above. Similarly to the liver slice (FIG. 3A), also in the hepatocyte spheroid (FIG. 3B), it is found out that the E-cadherin is concentrated between the cells. Also, similarly to the E-cadherin, it is found out that the actin is also localized in a portion of the cell membrane in both of the liver slice (FIG. 3D) and the spheroid (FIG. 3E) to undercoat the cell membrane. On the other hand, the conventional plane culture shows that the E-cadherin expressed in the living liver tissue is under the detectable limit (FIG. 3C) and also that actin stress fibers are tensed (FIG. 3F), and it is found out that its structure is obviously different from an essential structure. As described above, by the spheroid culture with using the NP sheet as compared with the conventional plane culture, the spheroid can be closer to that of the living tissue in the viewpoint of the structure. As described above, from the results in the culture with using the NP in which the actin stress fibers are not tensioned and the expression of the E-cadherin is detected, it appears that the intercellular (cell-cell) adhesion exceeds the cell-medium adhesion, and therefore, the three-dimensional steric structure in which the cell-cell adhesion is developed is formed.

<Ammonia Metabolic Capacity Measurement>

Next, in order to verify the function of the spheroid having the structure close to that of the living body, ammonia metabolic capacity which is an important function of the liver is measured.

Inside the living body, ammonia is mainly produced in the intestine and kidney and is carried to the liver by the bloodstream, and then, the liver converts the ammonia into urea with using the urea cycle. In order to measure the ammonia metabolic capacity of such a liver, a commercially-available dedicated kit is used. First, as following the above-described method, the hepatocyte spheroid is formed by the NP normal culture with using the 2.0 NP sheet. For comparison, the culture is performed as following the above-described plane culture method. In both culture, the medium is replaced with an ammonia culture medium in 72 hours after the start of the culture, and a part of the culture medium is sampled. After the culture for 24 hours from the replacement of the culture medium, the culture medium is similarly sampled. For each sampling liquid, a sample is prepared as following the descriptions of the kit. The absorbance at 630 nm is measured to calculate an amount of ammonia reduction (metabolism) over the 24 hours. Note that, with using a sample whose ammonia concentration is already known, a calibration curve is previously required. Meanwhile, for measuring the number of cells at the sampling, the cells are solubilized by SDS, and then, "Hoechst332582" is added thereto, and its fluorescence intensity is measured to obtain the number (excitation wavelength: 355 nm, fluorescence wavelength: 460 nm). While the commercially-available kit is employed in this example, any method is possible.

Figure 4:
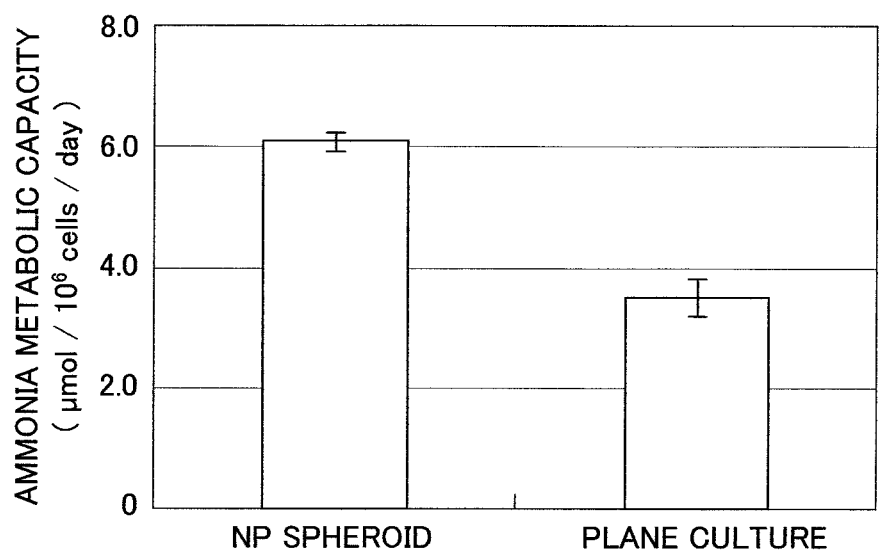
FIG. 4 is a diagram showing an ammonia metabolic capacity.

From a result of the measurement of the ammonia metabolic capacity of the spheroid having the three-dimensional structure reconstructed with using the NP sheet as described above, the capacity in the NP spheroid is dominantly higher than that of the conventional plane culture, and therefore, it is found out that the ammonia metabolism is actively boosted (FIG. 4). It is considered that, by forming the structure close to the essential structure of the hepatocyte, a polarity which is essentially preserved in the hepatocyte inside the living body is recovered at the same time, and the recovery results in the improvement of the function.

<Study on Bile Canalicular Excretion>

In order to verify the liver function of the spheroid formed with using the NP, an excretion capacity to the bile canaliculi which is one of the important functions of the liver is measured. In this example, the presence/absence of the excretion to the bile duct is verified by dosing 5-carboxy-2',7'-dichlorofluorescein diacetate (CDFDA) which is a substrate of the MRP2 which is a protein localized on the cell membrane forming the bile canaliculi. When the MRP2 has the activity, the CDFDA is excreted to the bile duct as 5-carboxy-2',7'-dichlorofluorescein (CDF).

A method of the measurement is performed as follows. First, as following the above-described method, the hepatocyte spheroid is formed by the NP normal culture with using the 2.0 NP sheet. For comparison, the sandwich culture (hereinafter, referred to as SW culture) which has advanced in the quantitative measurement of the biliary excretion is employed. The SW culture is performed as follows. The hepatocytes are suspended and seeded in the above-described culture medium at a density of $1 \times 10^5$ cells/ml on a commercially-available collagen-coated culture dish. The culture is started, the first culture-medium replacement is performed in 4 hours, the culture medium is replaced in 24 hours with a culture medium containing a biological matrix (hereinafter, referred to as biological-matrix culture medium), and then, the culture medium is replaced every 24 hours as following the above-described method for the culture (see FIG. 5K for a schematic diagram). In both culture, the measurement is performed in 24, 48, 72, and 96 hours after the start of the culture. At each time, the cells are washed once with the Hanks' solution (containing $Ca^{2+}$ and $Mg^{2+}$), the culture medium is replaced with a culture medium containing the CDFDA, and then, the sample is incubated at 37° C. for 20 minutes. The sample is washed three times with the Hanks' solution (containing $Ca^{2+}$ and $Mg^{2+}$), and is observed by a fluorescence microscope. The measurement is not necessarily limited to the conditions. Also, while an example that the MATRIGEL® or others is used as the biological matrix is described here, it is obvious that the substance is not limited to this.

As a result of the measurement, at the time of 24 hours, in both of the NP spheroid culture and the SW culture, an aspect that the uptake CDFDA is accumulated inside the cells is observed (in FIGS. 5A and 5F). It is considered that this is because no bile duct is formed for 24 hours after the seeding, or because, even if it is formed, the functional MRP2 is not expressed in a portion of the bile duct. Then, at the time of 48 hours, the CDFDA is accumulated both in the cells and the bile duct (FIGS. 5B and 5G). At the time of 72 hours (FIGS. 5C and 5H) and 96 hours (FIGS. 5D, 5E, 5I, and 5J), the CDFDA does not remain in the cells and is excreted to the bile duct. It is considered that this is because the bile duct is formed gradually with passing the time and the CDFDA is excreted to the bile duct as the CDF. As a result, it is found out that the bile duct is formed also in the NP spheroid similarly to the SW method, and that the functional MRP2 is localized in the bile duct.

<Real-Time PCR>

In order to verify that the formed spheroid maintains the high-dimensional structure as that of the liver tissue or has a liver-specific function, quantitative gene-expression analysis is performed with using the real-time PCR method. An expression level of a target gene of a hepatocyte obtained immediately after its collection is measured (Table 1), and, with taking the expression level as 1, an expression level under each culture condition is calculated, so that the expression levels are compared with each other.

TABLE 1

| Gene | Size (bp) | Catalog ID |
|------|-----------|------------|
| TBP | 153 | Rn01455648_m1 |
| E-cadherin | 105 | Rn00580109_m1 |
| MRP2 | 60 | Rn00563231_m1 |
| Claudin 3 | 90 | Rn00581751_s1 |
| P450-3A3 | 113 | Rn01640761_gH |
| Albumin | 95 | Rn00592480_m1 |

Figure 6A:
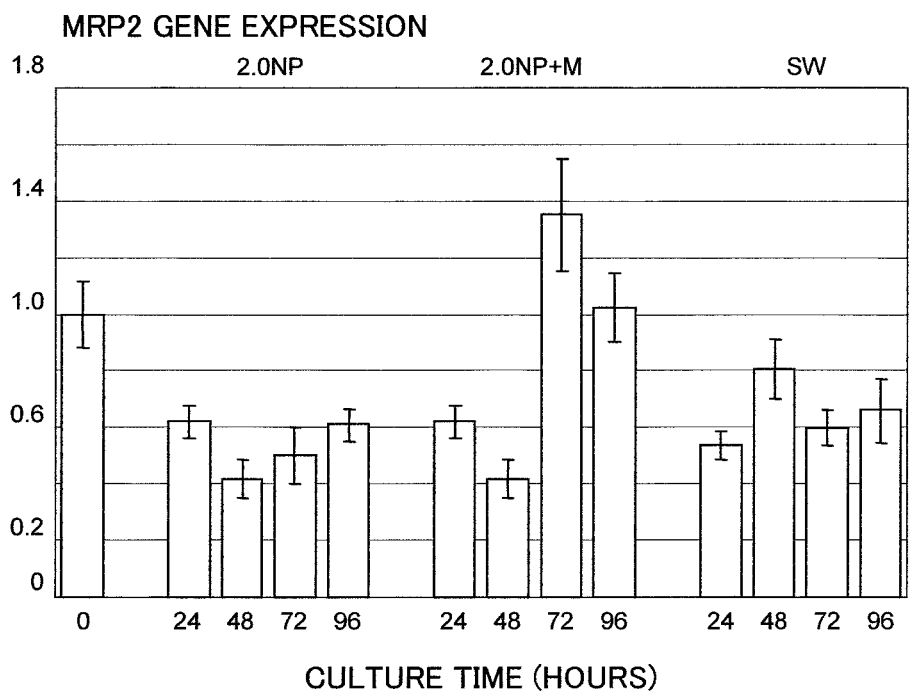
FIGS. 6A and 6B are diagrams showing results of gene-expression analysis with using real-time PCR.
Figure 6B:
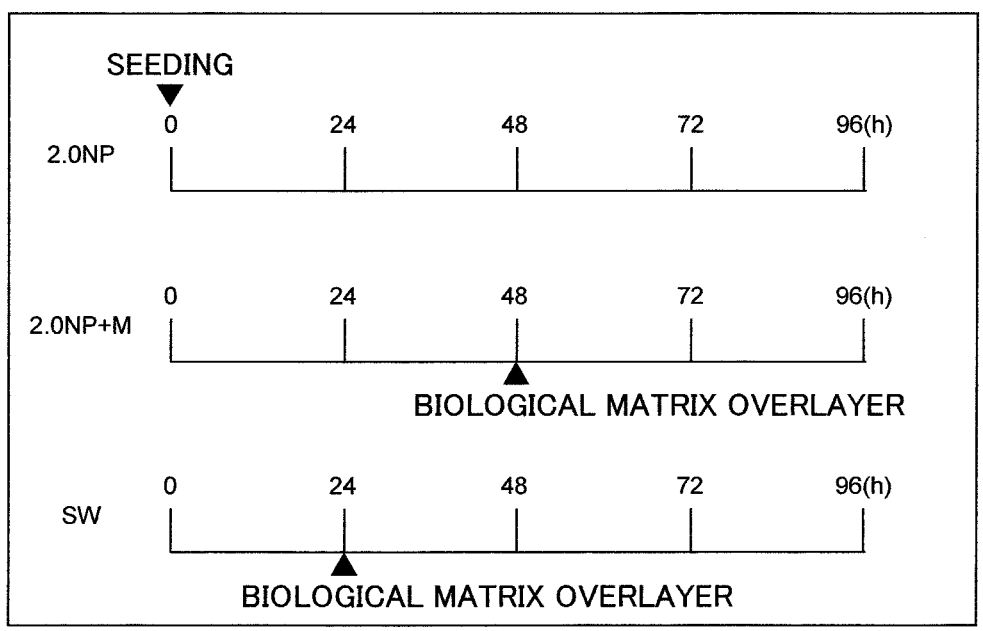

The expression levels are compared among three types of culture conditions (FIG. 6B). The first one is the NP normal culture on the above-described 2.0 NP (2.0 NP in FIG. 6B). The second one is a condition of overlayering the biological matrix in 48 hours after the seeding of the hepatocytes on the 2.0 NP (hereinafter, referred to as NP biological-matrix-overlayered culture, 2.0 NP+M in FIG. 6B). The biological matrix is an extracted component from an extracellular matrix, and has been used as the one of providing an environment closer to the living body in cellular biological experiments. Also, even in the above-described SW method, by using the biological matrix, the liver function can be improved. From these aspects, it is considered that, by applying the biological matrix to the NP spheroid, higher effects can be expected. At the same time, from the past studies with using a cell line, it is found out that a spheroid whose size is too large (its diameter is 50 µm or larger) is disadvantageous in points of osmosis (permeability) of a culture-medium component and supply of oxygen, and therefore, the spheroid is necrotized from its inside. Therefore, it is considered that the maintaining of the spheroid diameter of 50 µm or smaller is also an important factor for the improvement of the function of the spheroid. As a result of the above-described preliminary studies, it is considered that a high function can be expected by overlayering the biological matrix, and besides, that the size of the spheroid may be controlled, and therefore, this method is employed. A specific method for the biological matrix overlayered culture is performed as follows. The hepatocytes are seeded onto the NP sheet on which $10^{-6}$% (W/V) of the Type I collagen is coated. The culture is started with using a culture medium (10% FCS+), the first culture-medium replacement is performed in 18 hours, and the culture medium is replaced with a non-serum culture medium (culture medium (10% FCS−) in 24 hours. In another 24 hours, the culture medium is replaced with a biological matrix culture medium, and then, the culture medium replacement is performed with using the culture medium (10% FCS−) every 24 hours, and the sample is cultured for 96 hours. And, the third one is the SW culture (SW in FIG. 6B).

A scheme of the experiment is shown in FIG. 6B. For such an obtained NP normal culture, NP biological matrix overlayered culture, and SW culture, the spheroids and the cells are recovered by trypsin treatment in 24, 48, 72, and 96 hours after the start of the culture, and are centrifuged at 1,500 rpm at 4° C. for 5 minutes. A total RNA is extracted with using a dedicated kit. A reverse transcription reaction is performed to 1.0 µg of the total RNA to obtain a cDNA sample. With using the obtained cDNA, the real-time PCR is performed. The TBP and the MRP2 are employed for an internal control (standard) gene and a target gene, respectively, and the expression level is defined as a relative value under each condition obtained when it is assumed that an expression level of the hepatocytes immediately after the collection is 1. As an analysis technique, while a $_{\Delta\Delta}Ct$ method (the method uses a theory that a one-cycle difference in detection causes a two-fold difference in an amount of an amplification product. Since it is not required to prepare a calibration curve, the method has a merit that many samples can be processed. The method is also referred to as comparative Ct method.) is employed, a calibration curve method is also possible.

As a result of the experiment, under the condition of 2.0NP+M that the biological matrix is overlayered on the NP spheroid (FIG. 5A), the MRP2 which is a liver-specific transporter shows a higher expression level than those of the 2.0 NP and the SW culture that the biological matrix is not overlayered. This does not simply suggest that only the overlayering of the biological matrix is effective, but also suggests that the previous forming of the spheroid by the hepatocytes is important.

Example 3

Figure 7:
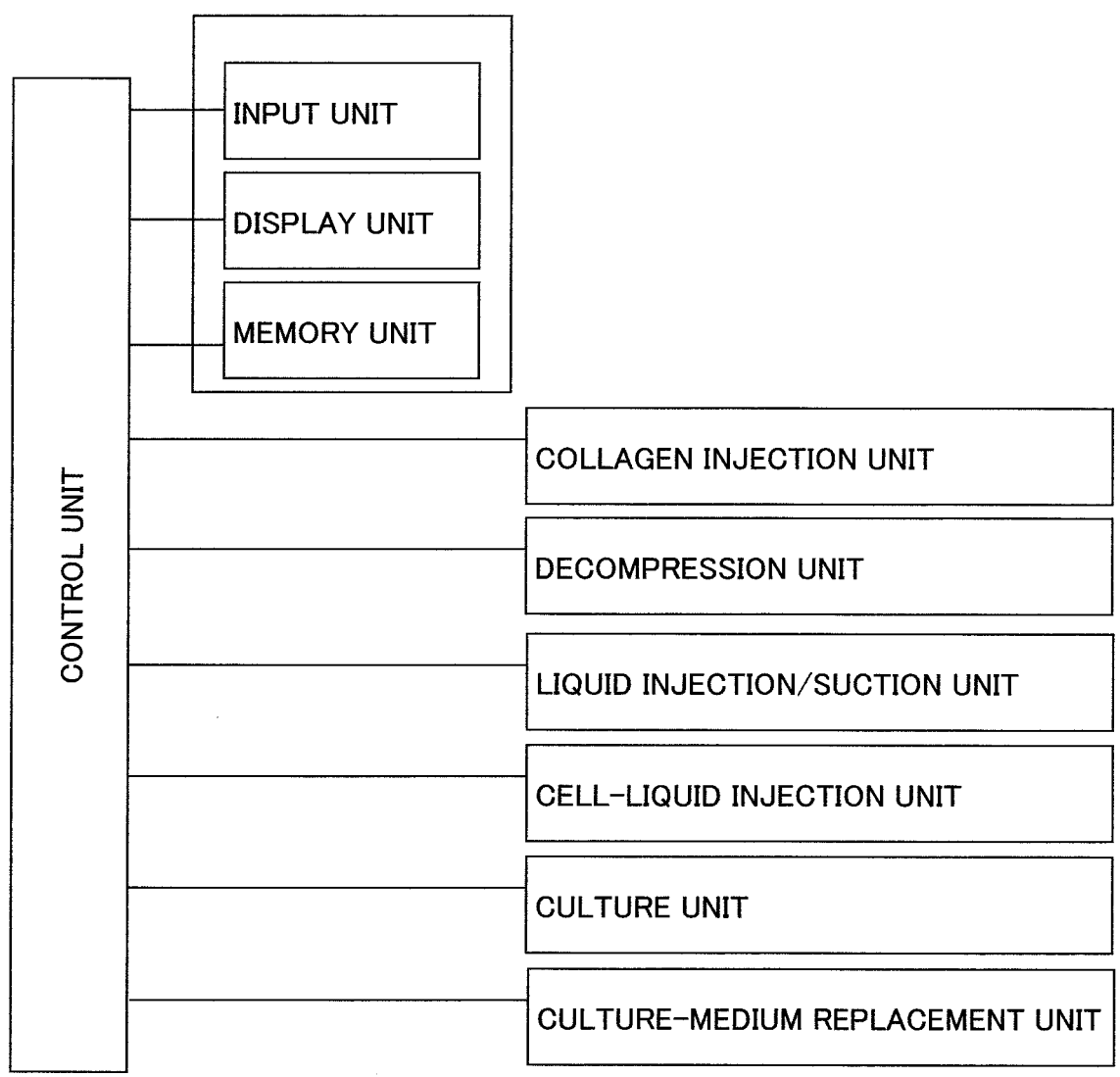
FIG. 7 is an entire configuration diagram of an automatic culture apparatus.

A configuration of the culture apparatus achieving the automation of the sequence of culture steps described in the Example 1 and its automatic culture steps are described below. FIG. 7 shows an entire configuration diagram of the automatic culture apparatus, FIG. 8 shows details of a decompression unit and a culture unit in the automatic culture apparatus, and FIG. 9 shows a culture automatic flowchart. The conditions are inputted by an input unit, and are displayed on a display unit. The inputted conditions include: an injection amount of the Type I collagen in a Type I collagen injection unit; a pressure inside a decompression chamber in the decompression unit; decompression time; a suction amount of a collagen liquid in a liquid injection/suction unit; an injection amount of a washing liquid; the number of washing times; an injection amount of a cell liquid in a cell suspension injection unit; a culture-unit temperature inside the culture unit; a $CO_2$ concentration inside the culture unit; culture time until the replacement of the culture medium (culture-medium replacement cycle); a culture-supernatant suction amount in a culture-medium replacement unit; a culture medium for the replacement; a culture-medium temperature for the replacement; an amount of the culture-medium replacement; total culture time for controlling both the culture unit and the culture-medium replacement unit; and others. On the display unit, these inputted information is displayed.

Also, by previously combining a plurality of conditions as the input conditions and storing them in a memory, the inputting can be simplified. The plurality of conditions are stored, and a condition under which the step is to be operated may be selected via the display unit.

The inputted information is transmitted to a control unit, and is stored in a memory or others. Based on the inputted information, a sequence of commands are invoked from the memory, so that the culture step is started. Note that an operation control for the culture step is collectively managed in a central processor mounted on the control unit. All steps are performed inside a clean room.

Further, a bar code, an RFID tag, or others is mounted on each culture dish, and a device for reading them is provided on each unit for executing the step, so that each step of the culture dish can be managed by electronic communications in the control unit.

The NP sheet is carried by a robotic arm, a belt conveyor, or other methods. Also, in a case that a part of the steps is independent in a separate apparatus, the culture dish may be carried in or out by an operator.

The culture dish on which the NP sheet is attached is first transferred to the type I collagen injection unit, and then, is put inside thereto from a carry-in/out part. A nozzle for injecting the Type I collagen into the culture dish is provided in the Type I collagen injection unit. An injection amount of the Type I collagen is previously stored in the memory, and an amount covering a projection tip portion of the NP sheet is preferable.

Figure 8A:
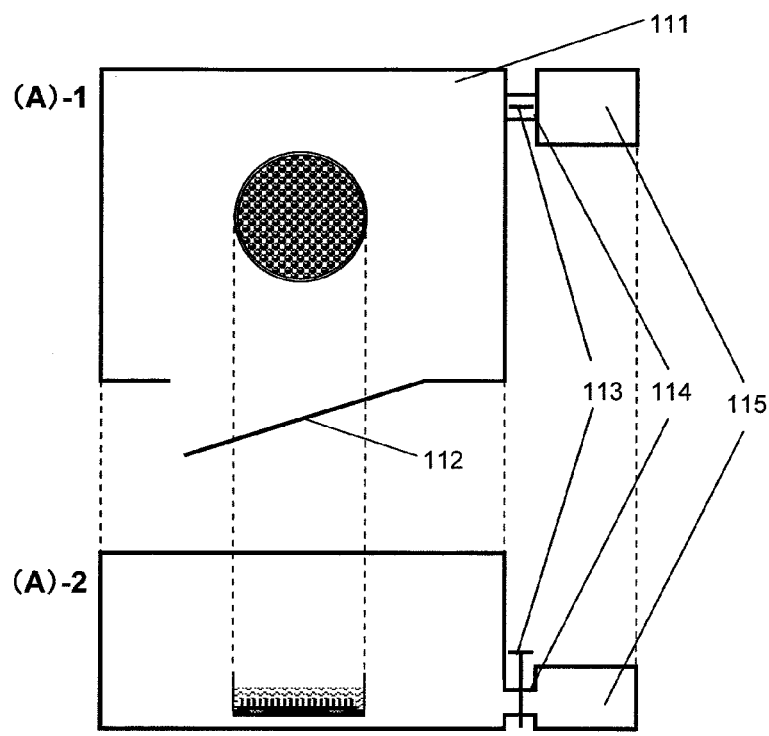
FIG. 8 is a diagram showing a decompression unit (A) and a culture unit (B) in the automatic culture apparatus.
Figure 9:
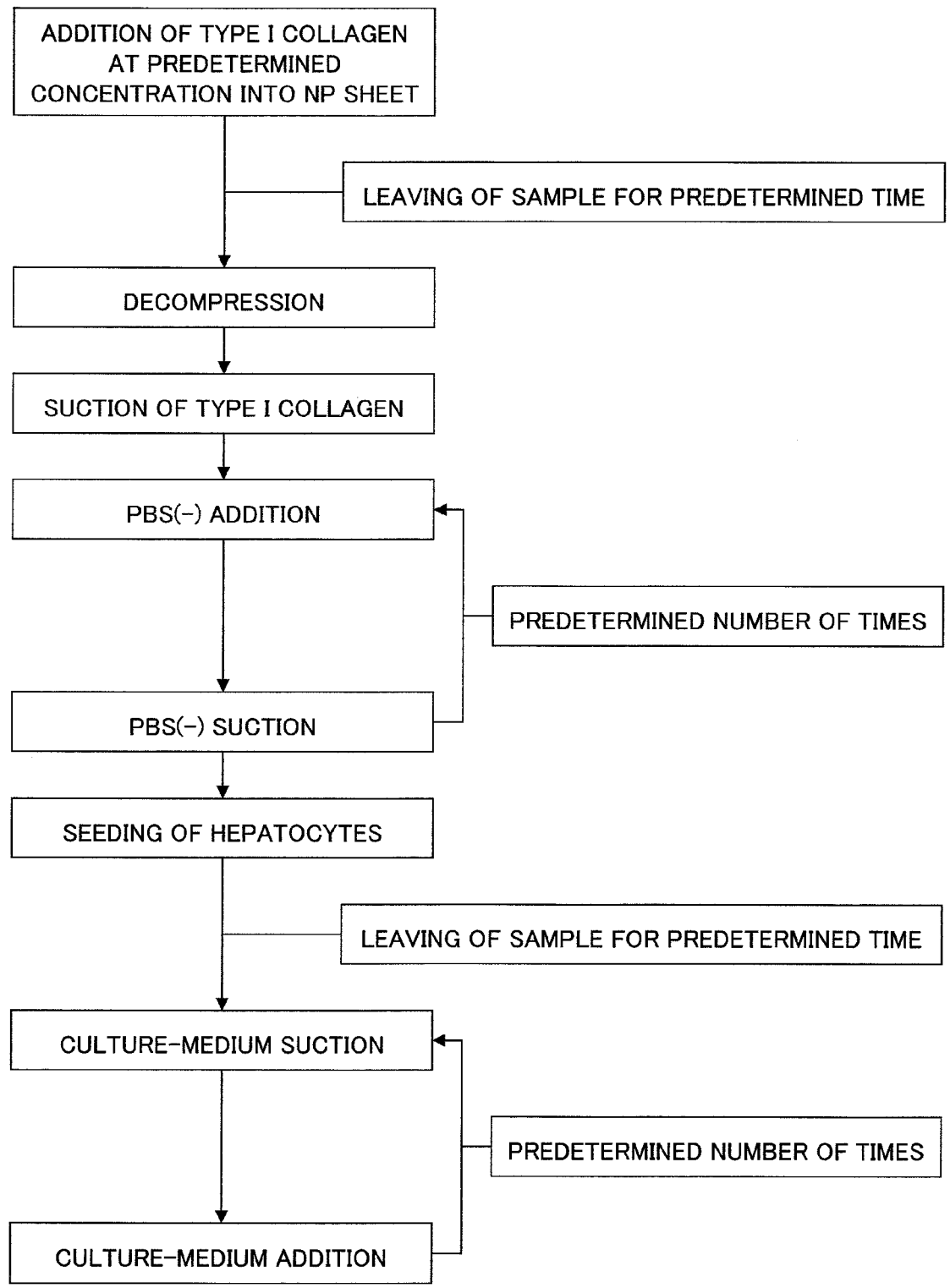
FIG. 9 is a flowchart showing the steps of culture automation.

The culture dish to which the Type I collagen has been injected is carried out from the carry-in/out part, and is subsequently transferred to the decompression unit (FIGS. 8A-1 and 8A-2, FIG. 8A-1 is a view as the decompression unit is seen from above, and FIG. 8A-2 is a view as the decompression unit is seen from a side). The culture dish is put from a carry-in/out part (112) of the decompression unit into a decompression chamber (111), and a door is closed. A decompression operation is controlled by the control unit. More specifically, after the culture dish is put into the chamber (111), an open/close valve (113) attached on a connection unit (114) between the decompression chamber and a decompression pump (115) is opened to decompress the pressure to 0.04 atm or lower. After the decompression for 10 minutes or longer, the open/close valve (113) is closed. After waiting until the pressure becomes about the same level as the atmospheric pressure, and the decompression operation is finished. After the decompression operation is finished by the open/close operations of the decompression pump, the door, and the valve, the culture dish is carried out from the carry-in/out part (112) of the decompression unit, and is transferred to the washing unit. In the washing unit, a suction device having a suction nozzle at its tip portion and a washing liquid having an injection nozzle at its tip portion are provided. While any washing liquid may be used, the PBS(−) is used in this example. Also, the tip portion of each nozzle has exchangeable means for preventing contamination. In the washing unit, after the suction of the Type I collagen liquid and the injection of the washing liquid, the suction and injection of the washing liquid are repeated a predetermined number of times. The injection amount and the number of washing times are previously stored in the memory.

After the washing operation is finished, the culture dish is transferred to the cell suspension injection unit. In the cell suspension injection unit, a cell suspension and a nozzle for injecting the cell suspension into the culture dish are provided. A predetermined amount previously stored in the memory is injected. Also, the cell suspension injection unit is configured such that its stage vibrates vertically and horizontally so as to evenly seed the injected cell suspension onto the culture dish. Further, a heat insulating material is provided in the cell suspension injection unit, and its temperature can be controlled by the control unit.

Figure 8B:
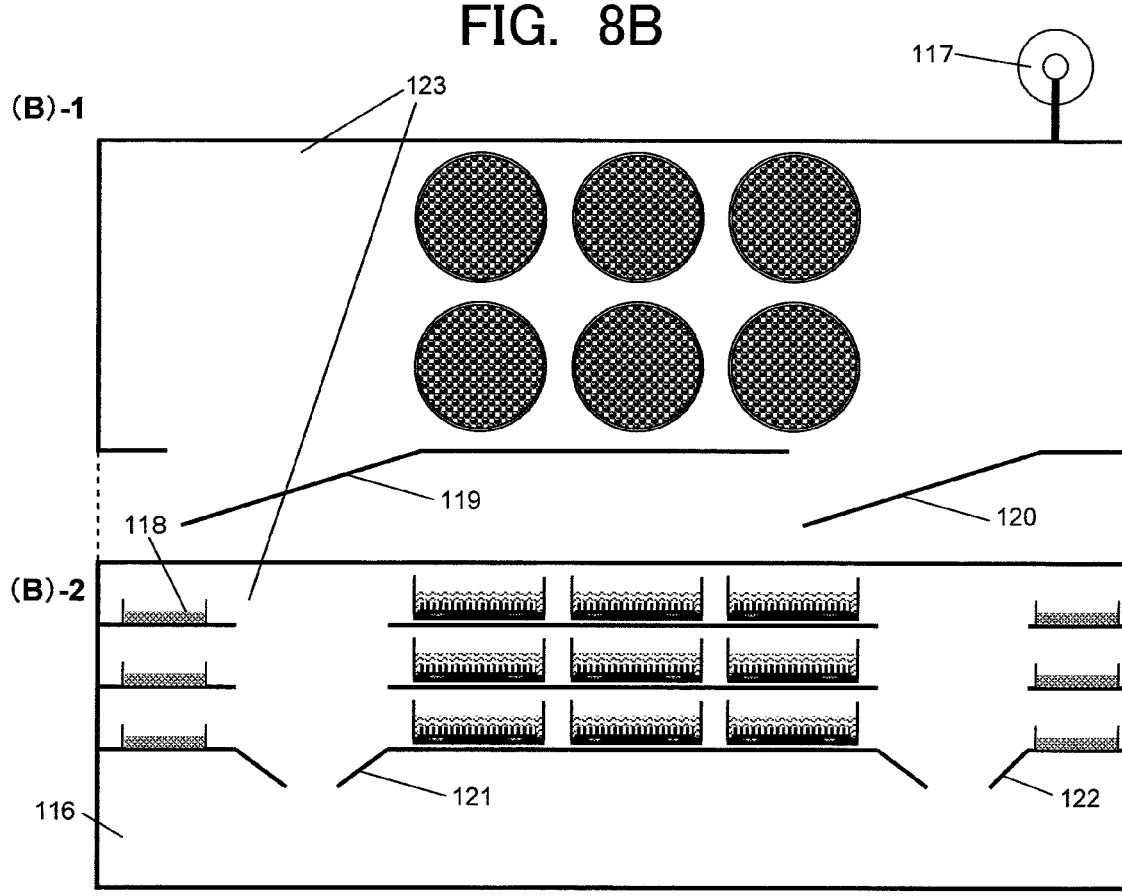

The culture dish to which the cell suspension has been injected (hereinafter, referred to as cultured cells) is subsequently transferred to the culture unit (FIG. 8B-1 and 8B-2, FIG. 8B-1 is a view as the decompression unit is seen from above, and FIG. 8B-2 is a view as the decompression unit is seen from a side). In the culture unit, a liquefied carbon dioxide gas tank (117) and a carbon dioxide monitor are provided in order to keep the $CO_2$ concentration inside an incubator (116) constant. Also, in order to keep the humidity inside the incubator constant, deionized water (118) is provided therein. By the control unit, the temperature control and time management can be achieved. The cultured cells having been transferred to the culture unit are transferred into the incubator from a carry-in part (119), and then, are transferred to a storage chamber (123) on an upper stage through an inner carry-in part (121). In the culture unit, by partitioning the inside of the incubator into two sections, a huge amount of the cultured cells can be cultured and the variation of the $CO_2$ concentration can be suppressed low. The cultured cells having been cultured for predetermined time are transferred to the culture-medium replacement unit through an inner carry-out part (122) and a carry-out part (120).

In the culture-medium replacement unit, a suction device having a suction nozzle at its tip portion and a culture medium having an injection nozzle at its tip portion are provided. The culture-medium replacement unit includes some chambers whose temperatures are controlled by the control unit, and the cultured cells are transferred to a culture-medium replacement chamber having a predetermined temperature in accordance with the intended use for the culture-medium replacement. The tip portion of each nozzle has exchangeable means for preventing contamination. The cultured cells having finished the culture-medium replacement are transferred to the culture unit again for the culture.

Each of the culture and the culture-medium replacement is performed a predetermined number of times for predetermined time, so that a desired spheroid can be obtained.

INDUSTRIAL APPLICABILITY

A monolayer culture on a two-dimensional plane has been a main stream of the cell culture. However, an in-vivo environment is three dimensional, and therefore, it is essential to form a cell culture system mimicking the environment and a cell group having a three-dimensional structure. In the present invention, by defining the concentration of the Type I collagen coated on the NP sheet, the spheroid which is the cell mass having such a three-dimensional structure can be easily formed. Besides, the spheroid formed by the present invention is a spheroid expressing the function close to that of the in-vivo liver tissue having the biliary excretion capacity, and its utility value in the drug discovery screening field is high.

The invention claimed is:

1. A method for culturing animal hepatocytes, comprising the steps of:
   coating a nanopillar sheet having spaces between nanopillars smaller than equivalent diameters of hepatocytes with a protein able to bind with integrin and comprising an extracellular matrix component containing Type I collagen having a Type I collagen concentration within a range of 100 pg/mL to 10 ng/mL;
   decompressing the nanopillar sheet on which the protein is coated;
   seeding hepatocytes, provided in a culture medium, onto the nanopillar sheet on which the protein is coated; and then
   replacing the culture medium after a period of time.

2. The method for culturing animal hepatocytes according to claim 1, wherein,
   wherein the step of seeding the hepatocytes comprises adhering the hepatocytes on the nanopillar sheet to form a hepatocyte spheroid.

3. The method for culturing animal hepatocytes according to claim 1, wherein
   the culture medium includes insulin and dexamethasone.

4. The method for culturing animal hepatocytes according to claim 3, wherein
a concentration of the insulin in the culture medium is within a range of 1 nM to 100 nM, and a concentration of the dexamethasone in the culture medium is within a range of 1 nM to 250 nM.

5. The method for culturing animal hepatocytes according to claim 1, wherein
a seeding density of the hepatocytes in the culture medium is $1\times10^4$ to $1\times10^6$ cells/ml.

6. The method for culturing animal hepatocytes according to claim 1, wherein,
after replacing the culture medium, a biological matrix is overlayered.

7. The method for culturing animal hepatocytes according to claim 6, wherein
the biological matrix contains a basement-membrane derived component.

8. The method for culturing animal hepatocytes according to claim 2, wherein
the hepatocyte spheroid has a diameter in a range of 30 to 100 μm.

9. The method for culturing animal hepatocytes according to claim 1, wherein
the period of time before which the culture medium is replaced is 4 hours to 24 hours.

* * * * *